United States Patent [19]

Klose et al.

[11] 4,282,001

[45] Aug. 4, 1981

[54] COMPOSITIONS AND METHOD FOR REDUCING TURBIDITY IN SAMPLES

[75] Inventors: Sigmar Klose, Berg; Herbert Buschek, Starnberg; Helmut Schlumberger, Polling, all of Fed. Rep. of Germany

[73] Assignee: Boehringer Mannheim GmbH, Waldhof, Fed. Rep. of Germany

[21] Appl. No.: 26,851

[22] Filed: Apr. 4, 1979

[30] Foreign Application Priority Data

Apr. 14, 1978 [DE] Fed. Rep. of Germany ....... 2816229

[51] Int. Cl.$^3$ ................... G01N 33/52; G01N 33/66; G01N 33/92
[52] U.S. Cl. ................... 23/ 230 B; 23/901; 23/909; 23/925; 252/174.22; 252/408
[58] Field of Search .......... 23/230 B; 252/408, 174.22

[56] References Cited

U.S. PATENT DOCUMENTS

| | | | |
|---|---|---|---|
| 3,853,465 | 12/1974 | Rush | 23/905 X |
| 3,958,939 | 5/1976 | Jones | 23/230 B |
| 4,148,869 | 4/1979 | Deaton | 23/230 B X |
| 4,154,706 | 5/1979 | Kenkare | 252/174.22 X |

*Primary Examiner*—Sidney Marantz

*Attorney, Agent, or Firm*—Sprung, Felfe, Horn, Lynch & Kramer

[57] ABSTRACT

For the removal of turbidities in reaction mixtures clouded by sample material, especially for photometric measurement, there are added to the reaction mixture:

(a) at least one low molecular weight organic compound, such as an aromatic alcohol or amine, which contains an electronegative substituent, for example a phenol or naphthol, which is substituted with one or more halogen atoms and/or hydroxyl groups and (b) at least one detergent which dissolves to give without compound (a), a clear solution and which forms a sparingly soluble complex with component (a), such as a non-ionic polyethylene oxide adduct or a cationic detergent, especially an alkyl, aralkyl or alkylthio ether or an alkyl or aralkyl ester of a polyethylene oxide glycol containing 8 to 22 carbon atoms in the alkyl radical and 5 to 25 ethylene oxide units or an alkyl dimethyl benzyl ammonium chloride compound containing 8 to 22 carbon atoms in the alkyl radical, in an amount sufficient for the appearance of a precipitate of the complex, whereafter further detergent is added thereto until the precipitated complex dissolves again.

12 Claims, No Drawings

COMPOSITIONS AND METHOD FOR REDUCING TURBIDITY IN SAMPLES

The present invention is concerned with a process and a reagent for the removal of turbidities in sample materials, such as biological sample materials.

Reagents to remove turbidity are useful in samples, e.g., serum or plasma-clouded reaction mixtures which are, inter alia, employed in clinical-chemical analysis and foodstuff analysis, as well as in water and effluent analysis. In order to achieve a higher specificity, enzymes are thereby frequently used.

A known problem in photometric analysis is the influence of turbidities of the sample, such as serum or plasma, on the analysis results when the measurement is carried out without sample blank value. The avoidance of the measurement of a sample blank value is desired in order to reduce the reagent consumption, to simplify the measurement and evaluation procedure and to reduce the amount of sample needed. In the case of the use of one-pot reagents, i.e. those containing a mixture of all the reaction components, in principle, the measurement of a sample blank value is even impossible. Such turbidities have various causes, a frequent cause being a high triglyceride content.

Turbidity leads to an increased inherent extinction in a sample-reagent mixture. Since the total extinction is made up of the colored component, which is directly proportional to the concentration of the substrate to be determined, and of a turbidity component, it follows that false results are hereby obtained.

It is known to clear such tubidities by the addition of detergents to such an extent that the turbidity component of the total extinction can be neglected (see German patent specification No. 2,327,894).

An important disadvantage of this process is the fact that very large amounts of detergent are needed. The necessarily high concentrations of detergent are disadvantageous since the activity of the enzymes employed is hereby frequently reduced and, furthermore, such amounts can frequently no longer be introduced into solid material mixtures which are to be dry and sprinklable. This is of particular importance in the case of one-pot reagents.

The present invention overcomes the above-mentioned disadvantages and provides a process and a reagent which permits the above-mentioned turbidities to be removed. By "removal" of turbidity is to be understood, within the scope of the invention, also the prevention or reduction of such turbidities.

The present invention provides a process for the removal of turbidities in reaction mixtures clouded by sample material, especially for photometric measurement by adding to the reaction mixture (a) at least one low molecular weight organic compound and (b) at least one detergent which dissolves to give a clear solution and which forms a sparingly soluble complex with the additive (a), in an amount sufficient to bring about the appearance of a precipitation of the complex, and then adding further detergent until the precipitated complex dissolves again.

The present invention is based upon the surprising discovery that the above-mentioned organic compounds, which themselves show, in a clear aqueous solution, no or only a very slight clarifying effect on the turbidities, synergistically extraordinarily increase the already known clarifying action of detergents. The result of this is that, in most cases, not only is a clarification made possible but also the turbidity can be completely removed and, at the same time, the amount of detergent necessary for this is drastically reduced. Examples of compounds (a) which can be used include:

(a) aromatic (condensed and non-condensed) alcohols and amines and preferably those which are strongly electronegatively substituted, preferred electronegative substituents being halogen atoms, for example benzyl alcohol, phenol, mono-, di- and trichlorophenols, di- and tribromophenols, cresols, naphthols, dihydroxynaphthols, aniline, chloroaniline and methylaniline;

(b) esters of aromatic acids and alkanoic acids, for example ethyl p-hydroxybenzoate, ethyl acetate, butyl acetate, ethyl propionate, ethyl trichloroacetate and the like;

(c) straight-chained, cyclic and branched aliphatic alcohols containing more than 3 carbon atoms, for example amyl alcohol, octanol, dodecanol, cyclohexanol and the like;

(d) halogenated, short-chained aliphatic compounds, for example dichloroethane, trichloroethylene, carbon tetrachloride, dichlorobutene, tetrachlorodifluoroethane and the like;

(e) aliphatic ketones, for example butan-2-one, cyclohexanone and the like;

(f) aldehydes, for example cinnamaldehyde and benzaldehyde;

(g) carboxylic acids, for example octanoic acid;

(h) ethers, for example 2-methoxyphenol;

(i) benzene.

The amount of such a compound (hereinafter called an adjuvant) for each particular case can be determined by preliminary experiments. In general, we have found that concentrations of from 0.5 to 300 mM and preferably of from 2 to 10 mM give good results.

The detergents forming sparingly soluble complexes with the above-mentioned adjuvants but which themselves dissolve clearly in the reaction mixture include the non-ionic, ionic and amphoteric detergents, non-ionic polyethylene oxide adducts being preferred. Especially good results are achieved with alkyl, aralkyl and alkylthio ethers, as well as with alkyl and aralkyl esters of polyethylene oxide glycols. In these detergents, the alkyl radicals generally contain 8 to 22 carbon atoms and the aryl radical is preferably a phenyl radical. The glycol residue of these detergents generally contains 3 to 25 ethylene oxide units in condensed form. Typical examples of this especially preferred group of detergents include thesit, Genapol, Tergitol, Triton X100, Lensodel and Brij 35. However, ionic detergents can also be employed, especially alkyl dimethyl benzyl ammonium chlorides, for the alkyl radical of which there applies that which is stated above with regard to the polyethylene oxide adducts. Secondary alkyl sulphates, the alkyl radicals of which also correspond to the above definition, have also proved to be useful. Of the amphoteric detergents, N-lauryldiethanolamide has proved to be useful.

Within the scope of the present invention, as already mentioned, the amount of detergent necessary is very considerably lowered in comparison with the previously known processes. In general, amounts of from 0.05 and 1% suffice, detergent additions of from 0.2 to 0.8% being preferred. Higher concentrations can, of course, also be used but here there is an increased danger of a negative effect on the enzymes. In contradistinction thereto, according to the above-mentioned German patent specification, 10 vol.% of detergent is employed for the clarification.

Especially low detergent concentrations can be used when dissolving of the complex of detergent and adjuvant is carried out by adding a detergent which is different from the detergent contained in the complex. In other words, in the case of this preferred embodiment of the present invention, at least two different detergents are employed. The second detergent used can also be one which is not able to form a sparingly soluble complex with the adjuvant, which can be recognised by a turbidity.

The present invention also provides a clarification agent for reaction mixtures for analysis processes which are clouded by sample material, especially for photometric measurement, with a content of detergent, wherein it consists of or contains (a) at least one low molecular weight organic compound and
(b) at least one detergent which dissolves to give a clear solution and which forms a less soluble complex with component (a) and optionally
(c) at least one further detergent which is different from (b) and which need not form sparingly soluble complex with (a).

For this clarification agent, there apply the above statements regarding the nature and amount of the detergents and adjuvants.

The process according to the present invention can be used in conjunction with all kinds of measurements in which turbidities can lead to a falsification or disturbance of the measurement and especially in the case of reaction mixtures which are intended for photometric measurement. Such reaction mixtures are well known and are, for example, described for many substances to be determined in "Methoden der enzymatischen Analyse", by H. U. Bergmeyer, pub. Verlag Chemie, Weinheim/Bergstrasse. Therefore, a more detailed explanation of such reaction mixture is here unnecessary.

The following Examples are given for the purpose of illustrating the present invention:

EXAMPLES 1 TO 36

Turbidity-clarifying systems

The following combinations according to the present invention gave, within 1 minute, up to a maximum of 2 hours, a removal of the turbidity in the system. 2 ml. test mixture +20 μl drinking milk with 3.5% fat content.

1 cm. optical path length 546 nm; 25° C.

(a) Variation of the adjuvant

In 0.1 M Tris/HCl buffer with 2% $MgSO_4.7H_2O$

| Example No. | Material | concentration | detergent conc.[1] | pH |
|---|---|---|---|---|
| 1 | 2,4-dichlorophenol | 8; 6; 4 mM | 5.6‰ | 8.0 |
| 2 | 2,3-dichlorophenol | 8; 6; 4mM | 2.8‰ | 8.0 |
| 3 | 2,4-dibromophenol | 8; 4 mM | 7.3‰ | 8.0 |
| 4 | phenol | 1%; 0.5% | 3.3% | 8.0 |
| 5 | 2,4,6-trichloro-phenol | 24; 12; 8 mM | 7‰ | 7.1 |
| 6 | 1,7-dihydroxy-naphthol | 8; 4 mM | 4.5‰ | 8.0 |
| 7 | 2,7-dihydroxy-naphthol | 8; 4 mM | 3.5‰ | 8.0 |
| 8 | 1,5-dihydroxy-naphthol | 8; 6; 4 mM | 5.5‰ | 8.0 |
| 9 | hydroquinone | 2% | 30‰ | 8.0 |
| 10 | aniline | 2: 1.5; 1 vol.% | 15‰ | 8.0 |
| 11 | 2-chloroaniline | 0.8 vol.% | 17‰ | 8.0 |
| 12 | o-toluidine | 1; 0.5 vol.% | 16‰ | 8.0 |
| 13 | pentan-1-ol | 2 vol.% | 9‰ | 8.0 |
| 14 | chloroform | 0.4 vol.% | 4‰ | 8.0 |
| 15 | benzene | 0.75 vol.% | 30‰ | 8.0 |
| 16 | guaiacol | 1 vol.% | 7‰ | 8.0 |
| 17 | benzaldehyde | 1 vol.% | 1.4‰ | 8.0 |
| 18 | cinnamaldehyde | 0.5 vol.% | 20‰ | 8.0 |
| 19 | cyclohexanone (with 6.0% $K_2SO_4$ and 2.5‰ Genapol Ox-80) in 0.5M potassium phosphate buffer | 3 vol.% | 1.2% | 8.0 |
| 20 | octanoic acid Na salt | 1‰ | 2.5‰ | 5.0 |

[1]hydroxypolyethoxydodecane (thesit)

(b) Variation of the detergent

In 0.1 M Tris/HCl buffer (ph 8.0) with 2% $MgSO_4.7H_2O$ and 8 mM/l. 2,4-dichlorophenol as additive, good clarification was achieved with the following systems:

| Example No. | Detergent I | Detergent II | conc. |
|---|---|---|---|
| 21 | thesit[2] | — | 5.6‰ |
| 22 | Tergitol NPX[3] | — | 10‰ |
| 23 | Triton X100[4] | — | 17‰ |
| 24 | Pegosperse[5] | — | 15‰ |
| 25 | thesit | Brij 35 | 2‰/2‰ |
| 26 | thesit | Tween 20 | 2‰/1‰ |
| 27 | thesit | benzalkonium chloride | 3.5‰/0.8‰ |
| 28 | Teepol 710[6] | Brij 35 | 5‰/7‰ |
| 29 | Lensodel Ab6[7] | Brij 35 | 5‰/12‰ |
| 30 | thesit | cetyl trimethyl ammonium bromide | 4‰/1‰ |
| 31 | Tween 20[8] | lauric acid-bis-(2-hydroxyethyl)-amine | 8‰/2‰ |
| 32 | Brij 35[9] | lauric acid-bis-(2-hydroxyethyl)-amine | 10‰/2‰ |
| 33* | Genapol 0 × 30[10] (in the presence of $K^+$ ions) | dodecyl sulphate Na salt | 3‰/16‰ |
| 34 | Tween 20 | cetyl trimethyl ammonium bromide | 7.5‰/1‰ |
| 35 | Genapol 0 × 80 | Tween 20 | 1‰/3.5‰ |
| 36* | Genapol 0 × 100[11] | dodecyl sulphate Na salt | 6‰/3‰ |

[2]see 1
[3]Tergitol NPX = 10,5-ethoxynonylphenol
[4]Triton X100 = 9,10-ethoxyoctylphenol
[5]Pegosperse = polyethyleneglycol lauryl ester
[6]Teepol 710 ⎫
[7]Lensodel AB6 ⎭ mixed $C_8$-$C_{18}$ sec.-alkyl sulphates
[8]Tween 20 = 20-ethoxy-sorbitan monolaurate
[9]Brij 35 = polyoxyethylene lauryl ether
[10]Genapol 0 × 80 ⎫ fatty alcohol polyglycol ether (straight-chained or branched-chained alcohol radicals with $C_{12}$ to $C_{15}$)
[11]Genapol X100 ⎭

EXAMPLE 37

Reagent for the determination of uric acid in serum

Formulation:

0.05 mol/l. $K_4P_2O_7$ 10 vol.% ethanol adjusted to pH 8.5 with HCl
1 mg./ml. NADP
1 U/ml. alcohol dehydrogenase EC 1.2.1.5
1000 U/ml. catalase EC 1.11.1.6
0.05 mol/l. disodium oxalate
0.05 mol/l. pyrazole Because of the given wavelength and the relatively high amount of sample necessary, in the case of lipaemically turbid sample material, the measurement is made difficult or impossible.

For the removal of this turbidity, the following additions were made:

(1)

2% butyl acetate
1.5% thesit (2)

0.5% dichloroethane
0.5% hexanol
5‰ Genapol X-80 (isotridecanol polyglycol ether)
9‰ Genapol X-100 (isotridecanol polyglycol ether)
6‰ thesit Test batch:
2 ml. reagent (with additives (1) or (2))
0.1 ml. sample
start with 0.6 U uricase EC 1.7.3.3.

Measurement at 340 nm and 25° C. to end point.

The effect of the above additives is that the initial extinctions, which are considerably increased by lipaemic, cloudy sample material, are broken down in a very short time.

A turbidity of about 2.0 is reduced within about 10 minutes to a stable level of about extinction 0.2 in comparison with the reagent blank value. It is thereby possible to balance in order to start the reaction.

EXAMPLE 38

Reagent for the determination of cholesterol in serum

Formulation:
2.54 g./l. KH$_2$PO$_4$
31.60 g./l. K$_2$HPO$_4$
8 g./l. Na$_2$SO$_4$
200 mg./l. 4-aminoantipyrin
282 mg./l. phenol
pH 7.90
3 U/ml. peroxidase EC 1.11.1.7
0.3 U/ml. cholesterol esterase EC 3.1.1.13
0.3 U/ml. cholesterol oxidase EC 1.1.3.6

The reagent is formulated as a one-pot mixture and must, therefore, be usable without measurement of a blank value. The fulfillment of this requirement is ensured, even in the case of strongly lipaemic, cloudy sample materials, by the following additives: Tubidity-clarifying additives:

(1)*

815 mg./l. 3,4-dichlorophenol
4 g./l. Genapol Ox-100
3 g./l. sodium desoxycholate (2)

2 g./l. heptanol
8 g./l. thesit (3)

1 g./l. ethyl acetate
7 g./l. thesit (4)

at pH 7.0 and 80 mM K$^+$/Na$^+$ phosphate buffer
1.5 g./l. ethyl p-hydroxybenzoate
4 g./l. thesit (5)* at pH 7.50 in 0.2 M potassium phosphate buffer in addition to the 3 mMol/l phenol needed for colour formation, also
35 mMol/l. phenol
1.5 g./l. Genapol Ox-100
1.5 g./l. Tween 20
1.0 g./l. sodium cholate Batch: 2 ml. reagent + 20 μl. sample, 546 nm, 25° C.

Turbidities of extinction $\geq 1.5$ caused by the sample material are broken down completely or to a negligible amount within the period of time needed for the reaction.

EXAMPLE 39

Reagent for the determination of glucose in serum

Formulation:
14.9 g./l. Na$_2$HPO$_4$
13.2 g./l. KH$_2$PO$_4$
8.0 g./l. Na$_2$SO$_4$
30 U/ml. glucose oxidase EC 1.1.3.4
1.8 U/ml. peroxidase EC 1.11.1.7
0.2 U/ml. esterase EC 3.1.1.13
470 mg./l. phenol
156 mg./l. 4-aminoantipyrin
at pH 7.0

Turbidity-clarifying additives:

(1)*

814 mg./l. 3,4-dichlorophenol
3.6 g./l. Genapol )x-100
3.0 g./l. tauroglycocholic acid (2)*

814 mg./l. 3,4-dichlorophenol
2.5 g./l. thesit
3.9 g./l. tauroglycocholic acid (3)* in 0.2 M potassium phosphate buffer, pH 7.0 additionally 1.35 g./l. phenol
489 mg./l. 3,4-dichlorophenol
3.0 g./l. Genapol Ox-100
2.8 g./l. sodium cholate Measurement here takes place at 578 nm. As already explained above in Example 38, the additives here result in the turbidities in the test batch caused by sample material being broken down in a very short period of time.

The above-given Examples contain those in which are used
(a) one or more detergents which dissolve to give a clear solution and which can form a sparingly soluble complex with the additional material; and those in which are used
(b) additionally to (a), at least one detergent which is not able to form a sparingly soluble complex with the additional material under the conditions in the reaction mixture (designated by *).

It will be understood that the specification and examples are illustrative but not limitative of the present invention and that other embodiments within the spirit and scope of the invention will suggest themselves to those skilled in the art.

What is claimed is:

1. Process for the removal of turbidity in aqueous reaction mixtures clouded by sample material, which method comprises adding to the reaction mixture
   (a) at least one low molecular weight organic compound selected from the group consisting of aromatic condensed and non-condensed alcohols and amines; esters of aromatic acids and alkanoic acids; straight-chained, cyclic and branched aliphatic alcohols containing more than 3 carbon atoms; halogenated, short-chained aliphatic compounds; aliphatic ketones aldehydes; carboxylic acids; ethers; and benzene and
   (b) at least one detergent which is capable of dissolving in the reaction mixture, in the absence of compound (a), to give a clear solution and capable of forming a sparingly soluble complex with said compound (a), and being selected from alkyl, aralkyl or alkylthio ether or an alkyl or aralkyl ester of a polyethylene oxide glycol containing 8 to 22 carbon atoms in the alkyl radical and 5 to 25 ethylene oxide units, in an amount sufficient to bring about the appearance of a precipitate of said complex, and then adding further detergent until the precipitated complex again dissolves.

2. Process as claimed in claim 1 wherein component (a) is an aromatic alcohol or amine containing an electronegative substituent.

3. Process as claimed in claim 1 wherein component (a) is a phenol or naphthol substituted with at least one halogen atom and/or hydroxyl group.

4. Process as claimed in claim 1 wherein component (a) is a di- or trihalophenol or dihydroxynaphthol.

5. Process as claimed in claim 1 wherein said detergent (b) used is a non-ionic polyethylene oxide adduct or a cationic detergent.

6. Process as claimed in claim 1 wherein the detergent (b) is an alkyl dimethyl benzyl ammonium chloride compound containing 8 to 22 carbon atoms in the alkyl radical.

7. Process as claimed in claim 1 wherein said further detergent added for dissolving the precipitated complex is different from the detergent contained in said precipitated complex.

8. Process as claimed in claim 1 wherein said further detergent added for dissolving the precipitated complex is the same as the detergent contained in said precipitated complex.

9. Process as claimed in claim 1 for clearing of serum or plasma samples preliminary to assay.

10. Composition for removing turbidity from serum or plasma-clouded reaction mixtures which composition comprises
    (a) at least one molecular weight organic compound selected from the group consisting of aromatic condensed and non-condensed alcohols and amines; esters of aromatic acids and alkanoic acids; straight-chained, cyclic and branched aliphatic alcohols containing more than 3 carbon atoms; halogenated, short-chained aliphatic compounds; aliphatic ketones; aldehydes; carboxylic acids; esters; and benzene and
    (b) at least one detergent capable of dissolving in the reaction mixture to give, without compound (a), a clear solution and capable of forming a sparingly soluble complex with said compound (a) and being selected from an alkyl, aralkyl, or alkylthio ether or an alkyl or aralkyl ester of a polyethylene oxide glycol and/or an alkyl dimethyl benzyl ammonium chloride or a mixture thereof and, optionally
    (c) at least one further detergent different from (b).

11. Composition as claimed in claim 10 wherein component (a) is an aromatic alcohol or amine containing an electro-negative substituent or a mixture thereof.

12. Composition as claimed in claim 10 containing at least one further detergent (c) which does not form a sparingly soluble complex with component (a).

* * * * *

UNITED STATES PATENT AND TRADEMARK OFFICE
CERTIFICATE OF CORRECTION

PATENT NO. : 4,282,001
DATED : August 4, 1981
INVENTOR(S) : Sigmar Klose, et al

It is certified that error appears in the above-identified patent and that said Letters Patent are hereby corrected as shown below:

On the title page, Item [73] should read:

"Boehringer Mannheim GmbH
Mannheim-Waldhof, Fed. Rep. of Germany"

Signed and Sealed this

Twentieth Day of April 1982

[SEAL]

Attest:

GERALD J. MOSSINGHOFF

*Attesting Officer*  *Commissioner of Patents and Trademarks*